US011517349B2

United States Patent
Pett et al.

(10) Patent No.: US 11,517,349 B2
(45) Date of Patent: Dec. 6, 2022

(54) AUTOVANCE FEATURE OF AN INTRAOSSEOUS DEVICE

(71) Applicant: Bard Access Systems, Inc., Salt Lake City, UT (US)

(72) Inventors: Daniel Pett, Sandy, UT (US); Daniel B. Blanchard, Bountiful, UT (US); Eric W. Lindekugel, Salt Lake City, UT (US); Joe Spataro, Cottonwood Heights, UT (US); Ralph Sonderegger, Farmington, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/031,650

(22) Filed: Sep. 24, 2020

(65) Prior Publication Data

US 2021/0093354 A1    Apr. 1, 2021

Related U.S. Application Data

(60) Provisional application No. 62/907,438, filed on Sep. 27, 2019.

(51) Int. Cl.
*A61B 17/34* (2006.01)
*A61B 17/16* (2006.01)
(Continued)

(52) U.S. Cl.
CPC ...... *A61B 17/3472* (2013.01); *A61B 17/1624* (2013.01); *A61B 17/3476* (2013.01);
(Continued)

(58) Field of Classification Search
CPC .......... A61B 2017/00367; A61B 17/16; A61B 17/1624; A61B 17/3472; A61B 17/3476; A61B 90/03; A61B 2090/034
See application file for complete search history.

(56) References Cited

U.S. PATENT DOCUMENTS

| 2,773,501 | A | 12/1956 | Young |
| 3,071,135 | A | 1/1963 | Baldwin et al. |

(Continued)

FOREIGN PATENT DOCUMENTS

| CN | 108742795 A | 11/2018 |
| CN | 110547847 A | 12/2019 |

(Continued)

OTHER PUBLICATIONS

PCT/US2019/ 018828 filed Feb. 20, 2019 International Preliminary Report on Patentability dated Aug. 27, 2020.

(Continued)

*Primary Examiner* — Larry E Waggle, Jr.
(74) *Attorney, Agent, or Firm* — Rutan & Tucker LLP

(57) ABSTRACT

Devices and methods for an autovance intraosseous device. The autovance intraosseous device can include a trigger activated system or pressure activated system that causes a needle to advance distally for a predetermined distance. The predetermined distance ensures a needle tip extends through the bone cortex, to access the medullary cavity, without penetrating a far wall of the medullary cavity. The advancement can be driven by a spring based system or an electric motor.

12 Claims, 6 Drawing Sheets

(51) Int. Cl.
 *A61B 90/00* (2016.01)
 *A61B 17/00* (2006.01)
(52) U.S. Cl.
 CPC ............... *A61B 2017/00367* (2013.01); *A61B 2090/034* (2016.02)

(56) References Cited

U.S. PATENT DOCUMENTS

| | | | |
|---|---|---|---|
| 3,804,544 A * | 4/1974 | Adams | A61B 17/16 408/14 |
| 3,811,442 A | 5/1974 | Maroth | |
| 3,815,605 A | 6/1974 | Schmidt et al. | |
| 3,991,765 A | 11/1976 | Cohen | |
| 4,266,555 A | 5/1981 | Jamshidi | |
| 4,314,565 A | 2/1982 | Lee | |
| 4,383,530 A | 5/1983 | Bruno | |
| 4,736,742 A | 4/1988 | Alexson et al. | |
| 4,889,529 A | 12/1989 | Haindl | |
| 4,952,207 A | 8/1990 | Lemieux | |
| 4,964,854 A | 10/1990 | Luther | |
| 4,969,870 A | 11/1990 | Kramer et al. | |
| 5,040,542 A | 8/1991 | Gray | |
| 5,042,558 A | 8/1991 | Hussey et al. | |
| 5,053,017 A | 10/1991 | Chamuel | |
| 5,122,114 A | 6/1992 | Miller et al. | |
| 5,207,697 A | 5/1993 | Carusillo et al. | |
| 5,263,939 A | 11/1993 | Wortrich | |
| 5,290,267 A | 3/1994 | Zimmermann | |
| 5,312,364 A | 5/1994 | Jacobs | |
| 5,332,398 A | 7/1994 | Miller et al. | |
| 5,364,367 A | 11/1994 | Banks et al. | |
| 5,372,583 A | 12/1994 | Roberts et al. | |
| 5,406,940 A | 4/1995 | Melzer et al. | |
| 5,451,210 A | 9/1995 | Kramer et al. | |
| 5,554,154 A | 9/1996 | Rosenberg | |
| 5,575,780 A | 11/1996 | Saito | |
| 5,591,188 A | 1/1997 | Waisman | |
| 5,601,559 A | 2/1997 | Melker et al. | |
| 5,667,509 A | 9/1997 | Westin | |
| 5,688,249 A | 11/1997 | Chang et al. | |
| 5,779,708 A | 7/1998 | Wu | |
| 5,817,052 A | 10/1998 | Johnson et al. | |
| 5,853,393 A | 12/1998 | Bogert | |
| 5,868,711 A | 2/1999 | Kramer et al. | |
| 5,885,293 A | 3/1999 | McDevitt | |
| 5,927,976 A | 7/1999 | Wu | |
| 5,960,797 A | 10/1999 | Kramer et al. | |
| 5,967,143 A | 10/1999 | Klappenberger | |
| 6,117,108 A | 9/2000 | Woehr et al. | |
| 6,135,769 A | 10/2000 | Kwan | |
| 6,199,664 B1 | 3/2001 | Tkaczyk et al. | |
| 6,210,373 B1 | 4/2001 | Allmon | |
| 6,228,088 B1 | 5/2001 | Miller et al. | |
| 6,247,928 B1 | 6/2001 | Meller et al. | |
| 6,270,484 B1 | 8/2001 | Yoon | |
| 6,273,715 B1 | 8/2001 | Meller et al. | |
| 6,419,490 B1 | 7/2002 | Kitchings Weathers, Jr. | |
| 6,458,117 B1 | 10/2002 | Pollins, Sr. | |
| 6,527,778 B2 | 3/2003 | Athanasiou et al. | |
| 6,602,214 B2 | 8/2003 | Heinz et al. | |
| 6,626,887 B1 | 9/2003 | Wu | |
| 6,629,959 B2 | 10/2003 | Kuracina et al. | |
| 6,641,395 B2 | 11/2003 | Kumar et al. | |
| 6,652,490 B2 | 11/2003 | Howell | |
| 6,692,471 B2 | 2/2004 | Boudreaux | |
| 6,761,726 B1 | 7/2004 | Findlay et al. | |
| 6,814,734 B2 | 11/2004 | Chappuis et al. | |
| 6,830,562 B2 | 12/2004 | Mogensen et al. | |
| 6,875,219 B2 | 4/2005 | Arramon et al. | |
| 6,905,486 B2 | 6/2005 | Gibbs | |
| 6,916,292 B2 | 7/2005 | Morawski et al. | |
| 6,984,213 B2 | 1/2006 | Horner et al. | |
| 6,997,907 B2 | 2/2006 | Safabash et al. | |
| 7,112,191 B2 | 9/2006 | Daga | |
| 7,135,031 B2 | 11/2006 | Flint | |
| 7,214,208 B2 | 5/2007 | Vaillancourt et al. | |
| 7,347,838 B2 | 3/2008 | Kulli | |
| 7,347,840 B2 | 3/2008 | Findlay et al. | |
| 7,407,493 B2 | 8/2008 | Cane' | |
| 7,458,954 B2 | 12/2008 | Ferguson et al. | |
| 7,513,888 B2 | 4/2009 | Sircom et al. | |
| 7,530,965 B2 | 5/2009 | Villa et al. | |
| 7,534,227 B2 | 5/2009 | Kulli | |
| 7,569,033 B2 | 8/2009 | Greene et al. | |
| 7,582,102 B2 | 9/2009 | Heinz et al. | |
| 7,588,559 B2 | 9/2009 | Aravena et al. | |
| 7,658,725 B2 | 2/2010 | Bialecki et al. | |
| 7,670,328 B2 | 3/2010 | Miller | |
| 7,699,807 B2 | 4/2010 | Faust et al. | |
| 7,699,850 B2 | 4/2010 | Miller | |
| 7,736,332 B2 | 6/2010 | Carlyon et al. | |
| 7,749,225 B2 | 7/2010 | Chappuis et al. | |
| 7,798,994 B2 | 9/2010 | Brimhall | |
| 7,811,260 B2 | 10/2010 | Miller et al. | |
| 7,815,642 B2 * | 10/2010 | Miller | A61B 17/3472 604/136 |
| 7,828,774 B2 | 11/2010 | Harding et al. | |
| 7,833,204 B2 | 11/2010 | Picha | |
| 7,842,038 B2 | 11/2010 | Haddock et al. | |
| 7,850,620 B2 | 12/2010 | Miller et al. | |
| 7,850,650 B2 | 12/2010 | Breitweiser | |
| D633,199 S | 2/2011 | MacKay et al. | |
| 7,899,528 B2 | 3/2011 | Miller et al. | |
| 7,905,857 B2 | 3/2011 | Swisher | |
| 7,951,089 B2 | 5/2011 | Miller | |
| 7,955,297 B2 | 6/2011 | Radmer et al. | |
| 7,972,339 B2 | 7/2011 | Nassiri et al. | |
| 7,976,502 B2 | 7/2011 | Baid | |
| 8,038,664 B2 | 10/2011 | Miller et al. | |
| 8,043,253 B2 | 10/2011 | Kraft et al. | |
| 8,043,265 B2 | 10/2011 | Abe et al. | |
| 8,142,365 B2 * | 3/2012 | Miller | A61B 10/025 600/566 |
| 8,152,771 B2 | 4/2012 | Mogensen et al. | |
| 8,162,904 B2 | 4/2012 | Takano et al. | |
| 8,167,899 B2 | 5/2012 | Justis et al. | |
| 8,235,945 B2 | 8/2012 | Baid | |
| 8,246,584 B2 | 8/2012 | Aravena et al. | |
| 8,273,053 B2 | 9/2012 | Saltzstein | |
| 8,292,891 B2 | 10/2012 | Browne et al. | |
| 8,308,693 B2 | 11/2012 | Miller et al. | |
| 8,333,769 B2 | 12/2012 | Browne et al. | |
| 8,356,598 B2 | 1/2013 | Rumsey | |
| 8,357,163 B2 | 1/2013 | Sidebotham et al. | |
| 8,388,541 B2 | 3/2013 | Messerly et al. | |
| 8,388,623 B2 | 3/2013 | Browne et al. | |
| 8,414,539 B1 | 4/2013 | Kuracina et al. | |
| 8,419,683 B2 | 4/2013 | Miller et al. | |
| 8,480,632 B2 | 7/2013 | Miller et al. | |
| 8,480,672 B2 | 7/2013 | Browne et al. | |
| 8,486,027 B2 | 7/2013 | Findlay et al. | |
| 8,506,568 B2 | 8/2013 | Miller | |
| 8,535,271 B2 | 9/2013 | Fuchs et al. | |
| 8,562,615 B2 | 10/2013 | Browne et al. | |
| 8,641,715 B2 | 2/2014 | Miller | |
| 8,647,257 B2 | 2/2014 | Jansen et al. | |
| 8,656,929 B2 | 2/2014 | Miller et al. | |
| 8,657,790 B2 | 2/2014 | Tai et al. | |
| 8,663,231 B2 | 3/2014 | Browne et al. | |
| 8,668,698 B2 | 3/2014 | Miller et al. | |
| 8,684,978 B2 | 4/2014 | Miller et al. | |
| 8,690,791 B2 | 4/2014 | Miller | |
| 8,715,287 B2 | 5/2014 | Miller | |
| 8,771,230 B2 | 7/2014 | White et al. | |
| 8,781,555 B2 | 7/2014 | Burnside et al. | |
| 8,801,663 B2 | 8/2014 | Woehr | |
| 8,812,101 B2 | 8/2014 | Miller et al. | |
| 8,814,835 B2 | 8/2014 | Baid | |
| 8,821,493 B2 * | 9/2014 | Anderson | A61B 90/06 606/80 |
| 8,828,001 B2 | 9/2014 | Stearns et al. | |
| 8,849,382 B2 | 9/2014 | Cox et al. | |
| 8,870,872 B2 | 10/2014 | Miller | |
| 8,936,575 B2 | 1/2015 | Moulton | |

(56) References Cited

U.S. PATENT DOCUMENTS

| | | |
|---|---|---|
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 * | 4/2017 | Nino ............... A61B 17/3494 |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csematoni |
| 10,052,111 B2 | 8/2018 | Miller et al. |
| 10,092,320 B2 | 10/2018 | Morgan et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| 10,893,887 B2 | 1/2021 | Blanchard |
| 10,980,522 B2 | 4/2021 | Muse |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsais et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2006/0015066 A1 | 1/2006 | Turieo et al. |
| 2006/0025723 A1 | 2/2006 | Ballarini |
| 2007/0049945 A1 | 3/2007 | Miller |
| 2007/0191772 A1 | 8/2007 | Wojcik |
| 2007/0270775 A1 | 11/2007 | Miller et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0188133 A1 | 7/2014 | Misener |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | Bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0022284 A1 | 1/2016 | Lele et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csematoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0092662 A1 | 4/2018 | Rioux et al. |

(56) References Cited

U.S. PATENT DOCUMENTS

| | | |
|---|---|---|
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0154112 A1 | 6/2018 | Chan et al. |
| 2018/0221003 A1 | 8/2018 | Hibner et al. |
| 2018/0242982 A1 | 8/2018 | Laughlin et al. |
| 2019/0069812 A1 | 3/2019 | Isaacson et al. |
| 2019/0282244 A1 | 9/2019 | Muse |
| 2020/0054347 A1 | 2/2020 | Coppedge et al. |
| 2020/0054410 A1 | 2/2020 | Pfotenhauer et al. |
| 2020/0113584 A1 | 4/2020 | McGinley et al. |
| 2020/0129186 A1 | 4/2020 | Miller et al. |
| 2020/0197121 A1 | 6/2020 | Morey et al. |
| 2021/0093357 A1 | 4/2021 | Pett et al. |
| 2021/0093358 A1 | 4/2021 | Lindekugel et al. |
| 2021/0322055 A1 | 10/2021 | Lindekugel et al. |
| 2021/0375445 A1 | 12/2021 | Lindekugel et al. |
| 2022/0240976 A1 | 8/2022 | Pett et al. |
| 2022/0249104 A1 | 8/2022 | Pett et al. |

FOREIGN PATENT DOCUMENTS

| | | |
|---|---|---|
| EP | 0923961 A1 | 6/1999 |
| ES | 2390297 A1 | 11/2012 |
| FR | 2581548 A1 | 11/1986 |
| JP | 2018509969 A | 4/2018 |
| WO | 1997024151 A1 | 7/1997 |
| WO | 1998052638 A3 | 2/1999 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 08033873 A2 | 3/2008 |
| WO | 2008033871 A2 | 3/2008 |
| WO | 2008033872 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 16033016 A1 | 3/2016 |
| WO | 16053834 A1 | 4/2016 |
| WO | 2016/085973 A1 | 6/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | WO-2018165334 A1 * | 9/2018 ......... A61B 17/1617 |
| WO | 2019051343 A1 | 3/2019 |
| WO | 2019/164990 A1 | 8/2019 |
| WO | 2021/011795 A1 | 1/2021 |
| WO | 2021/016122 A1 | 1/2021 |
| WO | 2021/062385 A1 | 4/2021 |
| WO | 2021062038 A1 | 4/2021 |
| WO | 2021062394 A1 | 4/2021 |
| WO | 2022/165232 A1 | 8/2022 |
| WO | 2022/170269 A1 | 8/2022 |

OTHER PUBLICATIONS

PCT/US2019/ 018828 filed Feb. 20, 2019 International Search Report and Written Opinion dated Jun. 13, 2019.

Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.

PCT/US2021/035475 filed Jun. 2, 2021 International Search Report and Written Opinion dated Sep. 17, 2021.

PCT/US2021/ 035232 filed Jun. 1, 2021 International Search Report and Written Opinion dated Oct. 19, 2021.

PCT/US2021/028114 filed Apr. 20, 2021 International Search Report and Written Opinion dated Jul. 12, 2021.

PCT/US2020/ 053119 filed Sep. 28, 2020 International Search Report and Written Opinion dated Jan. 5, 2021.

PCT/US2020/052558 filed Sep. 24, 2020 International Search Report and Written Opinion dated Feb. 11, 2021.

PCT/US2020/053135 filed Sep. 28, 2020 International Search Report and Written Opinion dated Dec. 18, 2020.

PCT/US2021/ 046573 filed Aug. 18, 2021 International Search Report and Written Opinion dated Nov. 30, 2021.

PCT/US2021/ 047378 filed Aug. 24, 2021 International Search Report and Written Opinion dated Nov. 17, 2021.

PCT/US2021/ 048542 filed Aug. 31, 2021 International Search Report and Written Opinion dated Dec. 9, 2021.

PCT/US2021/ 049475 filed Sep. 8, 2021 International Search Report and Written Opinion dated Dec. 9, 2021.

PCT/US2022/014391 filed Jan. 28, 2022 International Search Report and Written Opinion dated Apr. 14, 2022.

PCT/US2022/015686 filed Feb. 8, 2022 International Search Report and Written Opinion dated May 25, 2022.

U.S. Appl. No. 17/035,336, filed Sep. 28, 2020 Restriction Requirement dated Jul. 26, 2022.

* cited by examiner

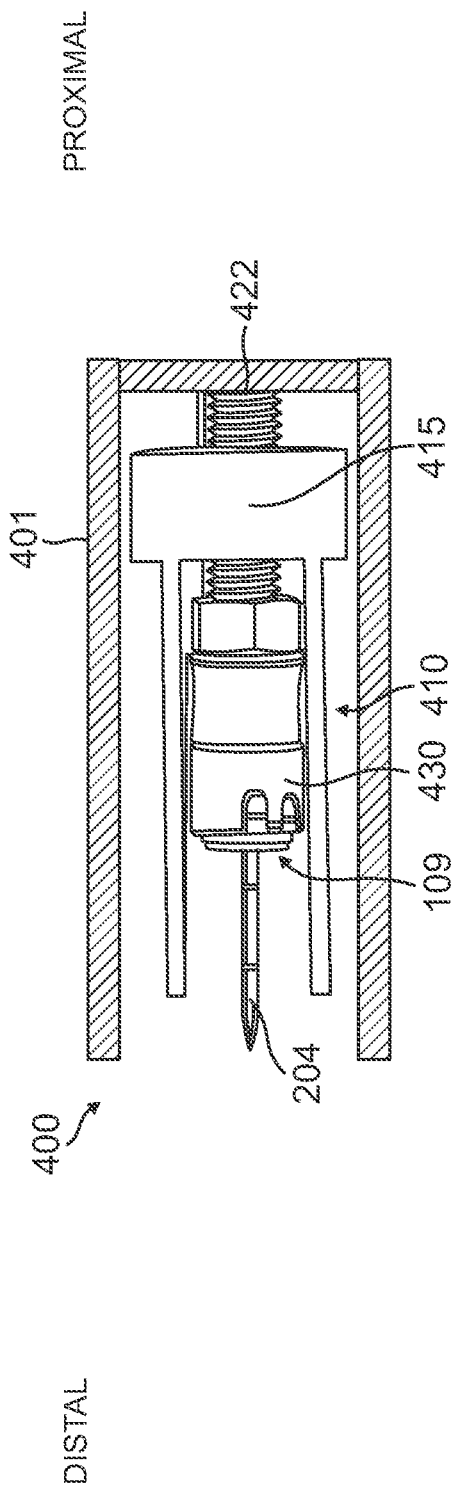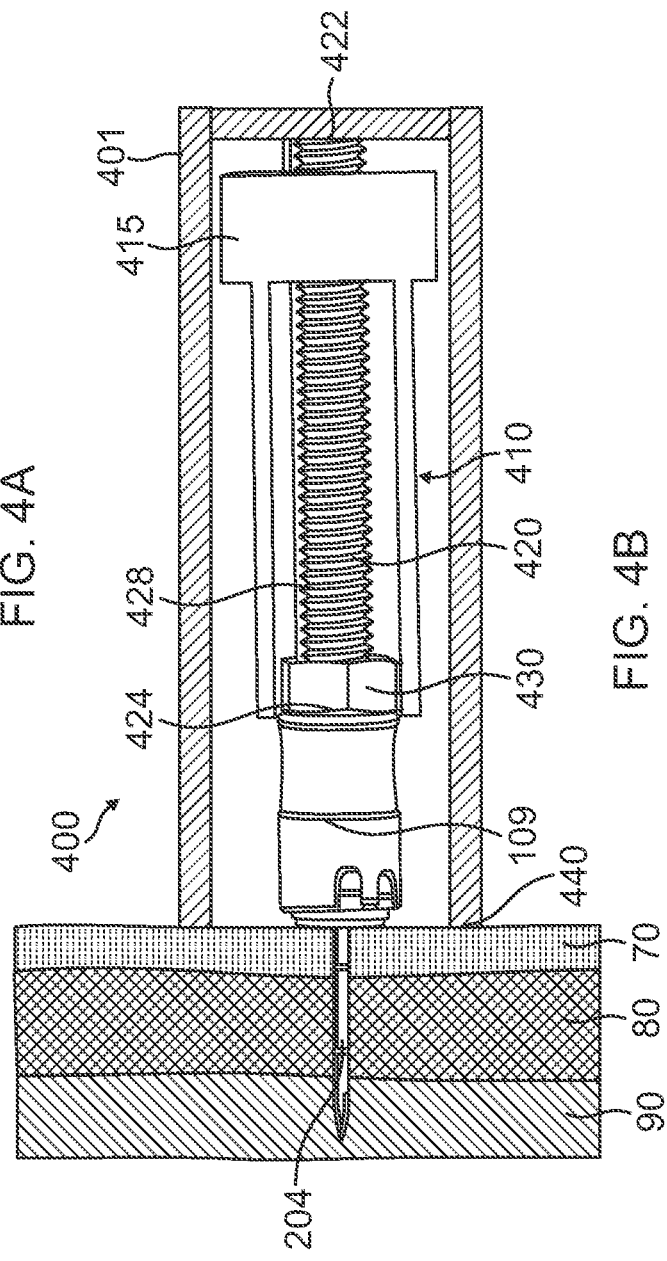

AUTOVANCE FEATURE OF AN INTRAOSSEOUS DEVICE

PRIORITY

This application claims the benefit of priority to U.S. Provisional Application No. 62/907,438, filed Sep. 27, 2019, which is incorporated by reference in its entirety into this application.

SUMMARY

Currently, inserting an intraosseous ("I.O.") needle often requires a powered drill, or similar powered device that, when activated, drives a needle through a bone layer to access the medullary cavity within. The clinician is required to selectively deactivate the device when they "feel" the needle advance past the relatively hard and compact, cortex layer of the bone and penetrates into the relatively soft, medullary cavity of the bone. However, the relative density of the bone cortex compared with the medullary cavity can vary depending on the bone, size of medullary space, and the patient, e.g. age, health, etc. Accordingly, the clinician relies on a subjective assessment of a lack of resistance in order to determine if the medullary cavity has been successfully accessed. Further, the clinician relies on a subjective assessment to ensure that the needle does not advance through the medullary space and penetrate the far wall of the medullary cavity.

Briefly summarized, embodiments disclosed herein are directed to apparatus and methods for an "autovance" intraosseous device. The device includes a trigger activated system or pressure activated system that causes a needle to advance distally a predetermined distance. The relative thickness of a bone cortex does not vary greatly between patients. Accordingly, the predetermined distance is sufficient to ensure a needle tip extends through the bone cortex, to access the medullary cavity, without penetrating a far wall of the medullary cavity. In some embodiments, the predetermined distance can be between 1 cm and 3 cm, however lesser or greater distances are also contemplated. The advancement can be driven by a spring based system or an electric motor.

Disclosed herein is an autovance intraosseous access device including, a housing, a drive screw, threadably engaged with the housing, the drive screw configured to advance a predetermined distance along a longitudinal axis, and an access assembly coupled to a distal end of the drive screw.

In some embodiments, the autovance intraosseous access device further includes a drive spring or an electric motor configured to rotate the drive screw. In some embodiments, the autovance intraosseous access device further includes a housing nut coupled with the housing in a fixed relationship and configured to threadably engage the drive screw with the housing. In some embodiments, the autovance intraosseous access device further includes a drive spindle rotatably coupled to the housing and slidably engaged with the drive screw to allow the drive screw to advance along the longitudinal axis.

In some embodiments, the autovance intraosseous access device further includes a locking piece coupled to the drive spindle and transitionable between a locked position to inhibit rotation of the drive spindle and an unlocked position to allow the drive spindle to rotate about the longitudinal axis. In some embodiments, a distal surface of the locking piece includes a protrusion, recess, detent, hex-key engagement, star ratchet engagement, or "lock and key" engagement, configured to engage a surface of the housing in the locked position. In some embodiments, the autovance intraosseous access device further includes a drive nut threadably engaged with the drive screw, slidably engaged with the housing and configured to engage the locking piece to transition the locking piece from the locked position to the unlocked position. In some embodiments, the autovance intraosseous access device further includes a drive screw head fixed coupled to a proximal end of the drive screw and configured to engage the housing to inhibit further longitudinal movement of the drive screw. In some embodiments, the predetermined distance is between 1 cm and 3 cm.

Also disclosed is an intraosseous access device including, a housing, a drive screw rotatably engaged with the housing and threadably engaged with an access assembly nut, the drive screw configured to advance the access assembly nut distally by a predetermined distance, and an access assembly coupled to a distal end of the access assembly nut.

In some embodiments, the intraosseous access device further includes a drive spring or an electric motor configured to rotate the drive screw. The drive spring or electric motor is actuated by a trigger actuator where a pressure is applied to the trigger or a pressure actuator where a pressure is applied to a distal tip of the access assembly. The access assembly nut is slidably engaged with the housing to allow longitudinal movement and to inhibit rotational movement of the access assembly nut. In some embodiments, the predetermined distance is between 1 cm and 3 cm.

Also disclosed is an intraosseous access device including, a housing, a drive screw fixedly engaged with the housing and threadably engaged with an access assembly nut, an access assembly coupled to a distal end of the access assembly nut, and an energy source configured to rotate the access assembly nut to advance the access assembly distally a predetermined distance.

In some embodiments, the energy source is a drive spring or an electric motor. The energy source is actuated by a trigger actuator, or a pressure actuator that is actuated when a longitudinal pressure is applied to the access assembly. In some embodiments, the predetermined distance is between 1 cm and 3 cm.

Also disclosed is an intraosseous access device including, a housing, a drive bolt slidably engaged with the housing along a longitudinal axis by a predetermined distance, a biasing member configured to urge the drive bolt distally, an access assembly coupled to a distal end of the drive bolt, and an energy source configured to transition the drive bolt between a locked position and an unlocked position.

In some embodiments, the energy source is a drive spring or an electric motor. The energy source is configured to rotate the drive bolt to transition the drive bolt between a locked position where longitudinal movement of the drive bolt is inhibited, and an unlocked position where the drive bolt can slide longitudinally. In some embodiments, the intraosseous access device further includes a protrusion engaging a surface of a bolt head of the drive bolt in the locked position and the protrusion aligning with a slot extending longitudinally through the bolt head in the unlocked position. The drive bolt engages a portion of the housing or a housing nut to inhibit further distal movement along a longitudinal axis. In some embodiments, the predetermined distance is between 1 cm and 3 cm.

Also disclosed is a method of accessing a medullary cavity including, actuating an energy source, rotating a drive screw, and advancing the drive screw, having an access assembly coupled thereto, a predetermined distance along a longitudinal axis.

In some embodiments, the method further includes actuating a trigger, or applying a longitudinal pressure to the access assembly, to actuate the energy source. In some embodiments, applying a longitudinal pressure to the access assembly includes sliding the drive screw proximally to transition a locking piece from a locked position to an unlocked position, the drive screw including a drive nut threadably engaged therewith and configured to abut against the locking piece. The locking piece engages a surface of a housing in the locked position, the locking piece including one of a protrusion, recess, detent, star ratchet engagement, hex-key engagement, or a "lock and key" engagement to inhibit movement relative to the housing.

In some embodiments, the method further includes rotating a drive spindle coupled to the locking piece, to rotate the drive screw, the locking piece configured to inhibit rotation of the drive spindle in the locked position and allow rotation of the drive spindle in the unlocked position. In some embodiments, a drive screw head, coupled to the drive screw, defines a facet that is slidably engaged with the drive spindle to allow longitudinal movement of the drive screw relative to the drive spindle, and to inhibit rotational movement of the drive screw relative to the drive spindle. The drive screw head engages one of a housing or a housing nut to inhibit further longitudinal movement. The energy source is one of a drive spring or an electric motor. In some embodiments, the predetermined distance is between 1 cm and 3 cm.

Also disclosed is a method of accessing a medullary cavity including, actuating an energy source, rotating a drive screw, and advancing an access assembly nut a predetermined distance along a longitudinal axis, the access assembly nut threadably engaged with the drive screw and including a facet that is slidably engaged with a housing and configured to inhibit rotational movement of the access assembly nut relative to the housing, the access assembly nut including an access assembly coupled to a distal end thereof.

In some embodiments, actuating an energy source includes actuating a trigger or applying a pressure to a distal tip of the access assembly. The energy source is one of a drive spring or an electric motor. In some embodiments, the predetermined distance is between 1 cm and 3 cm.

Also disclosed is a method of accessing a medullary cavity including, actuating an energy source, rotating an access assembly nut including an access assembly coupled to a distal end thereof, the access assembly threadably engaged with a drive screw, and advancing the access assembly a predetermined distance along a longitudinal axis.

In some embodiments, actuating an energy source includes actuating a trigger or applying a pressure to a distal tip of the access assembly. The energy source is one of a drive spring or an electric motor. In some embodiments, the predetermined distance is between 1 cm and 3 cm.

Also disclosed is a method of accessing a medullary cavity including, actuating an energy source, rotating a drive bolt to an unlocked position, and urging the drive bolt distally a predetermined distance, the drive bolt including an access assembly coupled to a distal end thereof.

In some embodiments, actuating an energy source includes actuating a trigger or applying a pressure to a distal tip of the needle. The energy source is one of a drive spring or an electric motor. In some embodiments, the method further includes a biasing member configured to urge the drive bolt distally. Rotating a drive bolt to an unlocked position includes aligning a slot extending longitudinally through a drive bolt head with a protrusion. The drive bolt head engages one of a housing or a housing nut to inhibit further longitudinal movement. In some embodiments, the predetermined distance is between 1 cm and 3 cm.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 4A-4B illustrate an intraosseous access system, in accordance with embodiments disclosed herein.

DESCRIPTION

Figure 1:
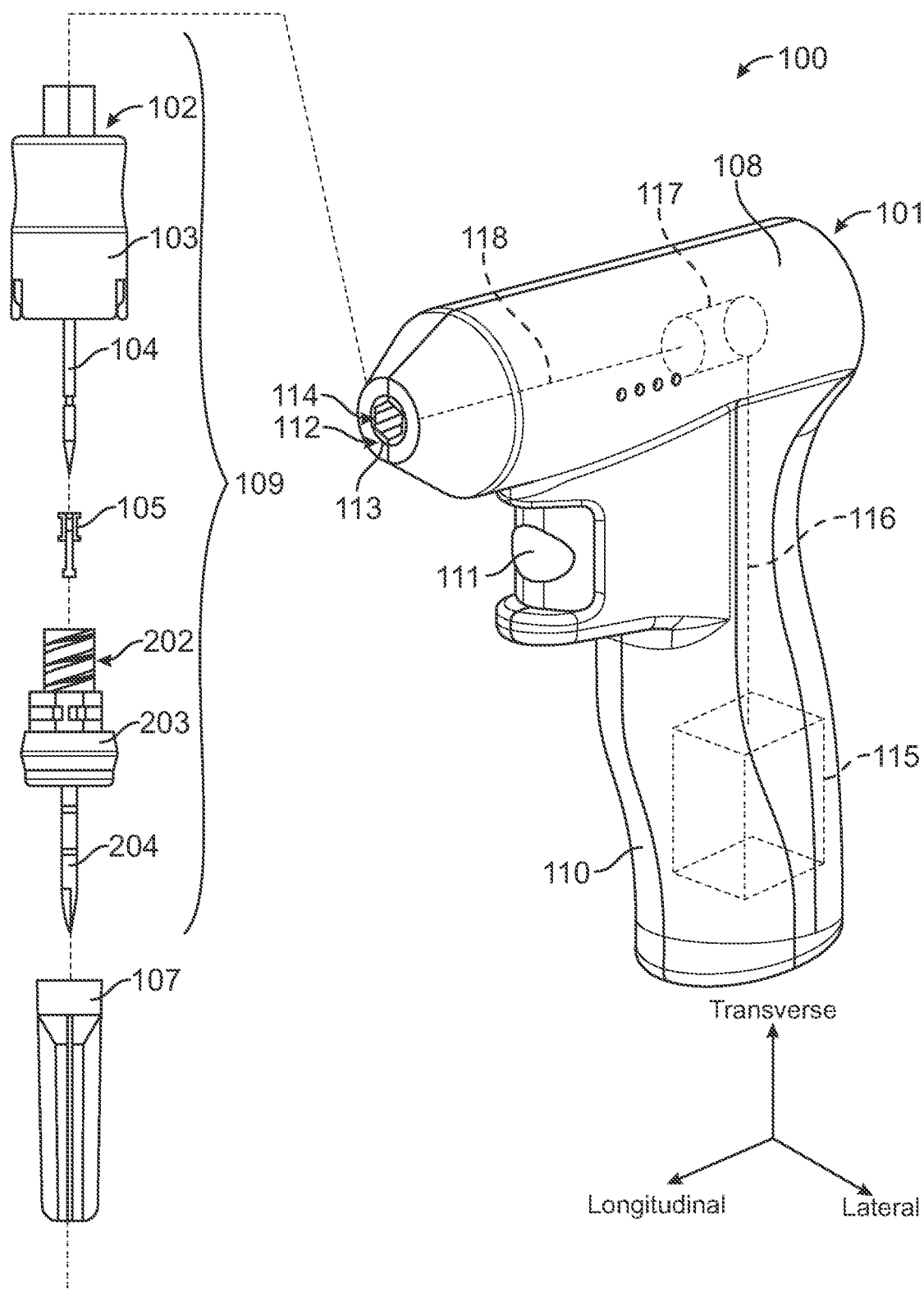
FIG. 1 illustrates an exploded view of an embodiment of an intraosseous access system, wherein an access assembly subset of the system is depicted slightly enlarged and in elevation, and an automated driver component is depicted in perspective, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

As shown in FIG. 1, and to assist in the description of embodiments described herein, a longitudinal axis extends substantially parallel to an axial length of a needle 204 extending from the driver 101. A lateral axis extends normal to the longitudinal axis, and a transverse axis extends normal to both the longitudinal and lateral axes. As used herein, the term "spring" can include any biasing member including compression springs, torsion springs, flat springs, or the like formed from metal, alloys, plastics, polymers, elastomers, rubber, silicone, composites, combinations thereof, or the like.

Unless defined otherwise, all technical and scientific terms used herein have the same meaning as commonly understood by those of ordinary skill in the art.

The present disclosure relates generally to intraosseous (10) access devices, systems, and methods thereof. FIG. 1 shows an exploded view of an exemplary embodiment of an intraosseous access system 100, with some components thereof shown in elevation and another shown in perspective. The intraosseous access system 100 can be used to penetrate skin and underlying hard bone for intraosseous access, such as, for example to access the marrow of the bone and/or a vasculature of the patient via a pathway through an interior of the bone.

In an embodiment, the system includes a driver 101 and an access assembly 109. The driver 101 can be used to rotate, or "drill," the access assembly 109 into a bone of a patient. In embodiments, the driver 101 can be automated or manual. In an embodiment, the driver 101 is an automated driver 108. For example, the automated driver 108 can be a drill that achieves high rotational speeds.

The intraosseous access system 100 can further include an obturator assembly 102, a shield 105, and a needle assembly 202, which may be referred to, collectively, as the access assembly 109. The access assembly 109 may also be referred to as an access system. The obturator assembly 102 is referred to as such herein for convenience. In an embodiment, the obturator assembly 102 includes an obturator 104. However, in some embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, and the like. Accordingly, the obturator assembly 102 may be referred to more generally as an elongated medical instrument assembly. In like manner, the obturator 104 may be referred to more generally as an elongated medical instrument.

In an embodiment, the obturator assembly 102 includes a coupling hub 103 that is attached to the obturator 104 in any suitable manner (e.g., one or more adhesives or overmolding, etc.). The coupling hub 103 can be configured to interface with the driver 101. The coupling hub 103 may alternatively be referred to as an obturator hub 103 or, more generally, as an elongated instrument hub 103.

In an embodiment, the shield 105 is configured to couple with the obturator 104. The coupling can permit relative longitudinal movement between the obturator 104 and the shield 105, such as sliding, translating, or other movement along an axis of elongation (i.e., axial movement), when the shield 105 is in a first operational mode, and can prevent the same variety of movement when the shield 105 is transitioned to a second operational mode. For example, as further discussed below, the shield 105 may couple with the obturator 104 in a manner that permits longitudinal translation when the obturator 104 maintains the shield 105 in an unlocked state, and when the obturator 104 is moved to a position where it no longer maintains the shield in the unlocked state, the shield 105 may automatically transition to a locked state in which little or no translational movement is permitted between the shield 105 and the obturator 104. Stated otherwise, the shield 105 may be longitudinally locked to a fixed or substantially fixed longitudinal orientation relative to the obturator 104 at which the shield 105 inhibits or prevents inadvertent contact with a distal tip of the obturator, as further discussed below. In various embodiments, the shield 105 may be configured to rotate relative to the obturator 104 about a longitudinal axis of the obturator 104 in one or more of the unlocked or locked states.

With continued reference to FIG. 1, the needle assembly 202 is referred to as such herein for convenience. In an embodiment, the needle assembly 202 includes a needle 204. However, in various other embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In an embodiment, the needle assembly 202 includes a needle hub 203 that is attached to the needle 204 in any suitable manner. The needle hub 203 can be configured to couple with the obturator hub 103 and may thereby be coupled with the driver 101. The needle hub 203 may alternatively be referred to as a cannula hub 203.

In an embodiment, the shield 105 is configured to couple with the needle hub 203. The coupling can prevent relative axial or longitudinal movement between the needle hub 203 and the shield 105, such as sliding, translating, or the like, when the shield 105 is in the first operational mode, and can permit the shield 105 to decouple from the needle hub 203 when the shield 105 is transitioned to the second operational mode. For example, as further discussed below, the shield 105 may couple with the needle hub 203 so as to be maintained at a substantially fixed longitudinal position relative thereto when the obturator 104 maintains the shield 105 in the unlocked state, and when the obturator 104 is moved to a position where it no longer maintains the shield in the unlocked state, the shield 105 may automatically transition to a locked state relative to the obturator 104, in which state the shield 105 also decouples from the needle hub 203.

In an embodiment, the shield 105 can be coupled with the obturator 104, the obturator 104 can be inserted into the needle 204, and the obturator hub 103 can be coupled to the needle hub 203 to assemble the access assembly 109. In an embodiment, a cap 107 may be provided to cover at least a distal portion of the needle 204 and the obturator 104 prior to use of the access assembly 109. For example, in an embodiment, a proximal end of the cap 107 can be coupled to the obturator hub 103.

With continued reference to FIG. 1, the automated driver 108 may take any suitable form. The driver 108 may include a handle 110 that may be gripped by a single hand of a user. The driver 108 may further include an actuator 111, e.g. trigger actuator, of any suitable variety via which a user may selectively actuate the driver 108 to effect rotation of a coupling interface 112. For example, the actuator 111 may comprise a button, as shown, or a switch or other mechanical or electrical element for actuating the driver 108. In an embodiment, the coupling interface 112 is formed as a socket 113 that defines a cavity 114. The coupling interface 112 can be configured to couple with the obturator hub 103. In an embodiment, the socket 113 includes sidewalls that substantially define a hexagonal cavity into which a hexagonal protrusion of the obturator hub 103 can be received. Other suitable connection interfaces are contemplated.

The automated driver 108 can include an energy source 115 of any suitable variety that is configured to energize the rotational movement of the coupling interface 112. For example, in some embodiments, the energy source 115 may comprise one or more batteries that provide electrical power for the automated driver 108. In other embodiments, the energy source 115 can comprise one or more springs (e.g., a coiled spring) or other biasing member that may store potential mechanical energy that may be released upon actuation of the actuator 111.

The energy source 115 may be coupled with the coupling interface 112 in any suitable manner. For example, in an embodiment, the automated driver 108 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage that mechanically transfers rotational energy from a mechanical (e.g., spring-based) energy source 115 to the gear assembly 117. The automated driver 108 can include a mechanical coupling 118 of any suitable variety to couple the gear assembly 117 with the coupling interface 112. In other embodiments, the gear assembly 117 may be omitted.

In embodiments, the automated driver 108 can rotate the coupling interface 112, and thereby, can rotate the access assembly 109 at rotational speeds significantly greater than can be achieved by manual rotation of the access assembly 109. For example, in various embodiments, the automated driver 108 can rotate the access assembly 109 at speeds of between 200 and 3,000 rotations per minute (rpm). However, it will be appreciated that lesser or greater rotational speeds are also contemplated.

Further details and embodiments of the intraosseous access system 100 can be found in WO 2018/075694, WO 2018/165334, WO 2018/165339, and US 2018/0116693, each of which is incorporated by reference in its entirety into this application.

In an embodiment, the intraosseous access system 100 further includes an advancement assembly disposed between the energy source 115 and the driver coupling interface 112, and operably coupled therewith. When the intraosseous access system 100 is activated, the advancement assembly advances the access assembly 109 a predetermined distance relative to the driver 101, through the longitudinal axis. Since the thickness of the bone cortex is similar between patients, advancing the access assembly 109 the predetermined distance will ensure the tip of the needle 204 advances sufficiently into the medullary cavity to provide access thereto, without impinging a far wall, termed "backwalling." In an embodiment, the predetermined distance can be between 1 cm and 3 cm, however lesser or greater distances are also contemplated.

In an embodiment, the intraosseous access system 100 is trigger activated, whereby once triggered by a user, the advancement assembly advances the access assembly 109 the predetermined distance before automatically stopping any further advancement. In an embodiment, the intraosseous access system 100 is pressure activated, for example when a pressure is exerted on the needle 204, such as when the needle is pressed against an outer wall of the bone. Once activated, the advancement assembly advances the access assembly 109 the predetermined distance before automatically stopping any further advancement.

Figure 2:
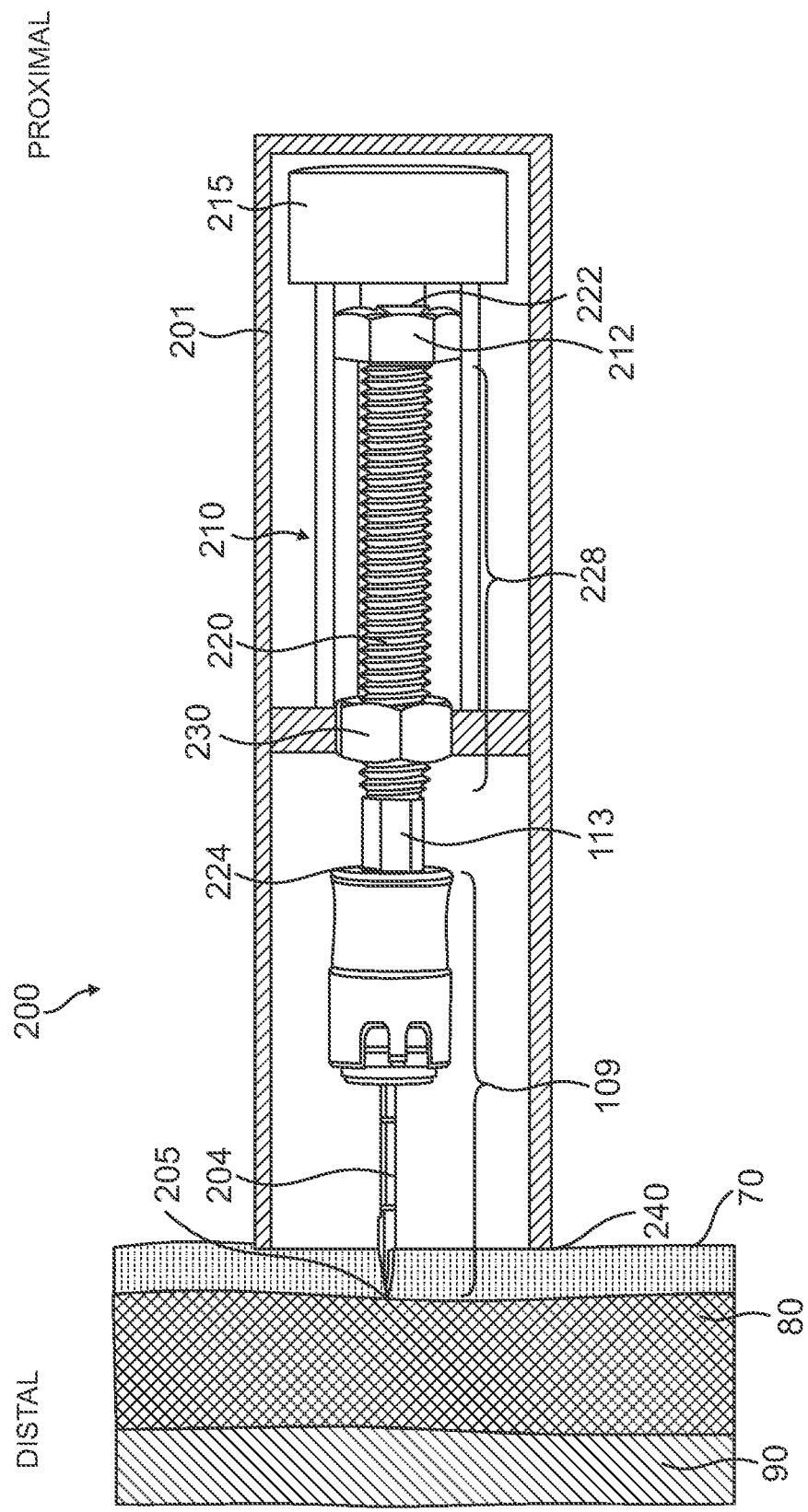
FIG. 2 illustrates an intraosseous access system, in accordance with embodiments disclosed herein.

FIG. 2 shows an embodiment of an intraosseous access system 200, including a driver 201, an energy source 215, and an advancement assembly 210. The advancement assembly 210 includes a drive screw 220 extending from a proximal end 222 to a distal end 224 and including a threaded portion 228, and a drive screw head 212 disposed at a proximal end thereof. The drive screw 220 is coupled with an energy source 215 such that the energy source 215 can cause the drive screw 220 to rotate about a longitudinal axis. As described herein the energy source 215 can be an electric motor, battery, torsion spring, combinations thereof, or the like, or similar electrically, chemically, or kinetically powered device that provides sufficient rotational speed and torque. It will be appreciated that the drive screw 220 and energy source 215 can be coupled by way of a gear mechanism, e.g. gear assembly 117.

The drive screw 220 is threadably engaged with a housing nut 230, or similar female threaded structure that engages the male threaded portion 228 of the drive screw 220. The housing nut 230 is fixedly coupled to the driver 201 so as to prevent any relative movement between the housing nut 230 and the driver 201. A distal end 224 of the drive screw 220 is coupled with a socket 113 that engages an access assembly 109. In use, a distal end 240 of the driver 201 is positioned against the skin surface 70 of the patient and the energy source 215 is activated. As discussed herein, the energy source is trigger activated, pressure activated, or combinations thereof. The energy source 215 rotates the drive screw 220, socket 113, and advancement assembly 109 together. The threaded portion 228 of the drive screw 220 engages the housing nut 230 and advances the drive screw 220, socket 113, and advancement assembly 109 in a distal direction relative to the driver 201.

The driver 201 continues to rotate the drive screw 220 until the drive screw head 212 contacts the housing nut 230 and prevents any further distal advancement. In an embodiment, the intraosseous access system 200 includes a switch that shuts off the energy source 215, e.g. an electric motor, when the drive screw head 212 advances a predetermined distance. It will be appreciated that the distance of distal travel of the drive screw 220 and access assembly 109 is sufficient to advance the tip 205 of the needle 204 through the cortex 80 of the bone to access the medullary cavity 90.

Figure 3:
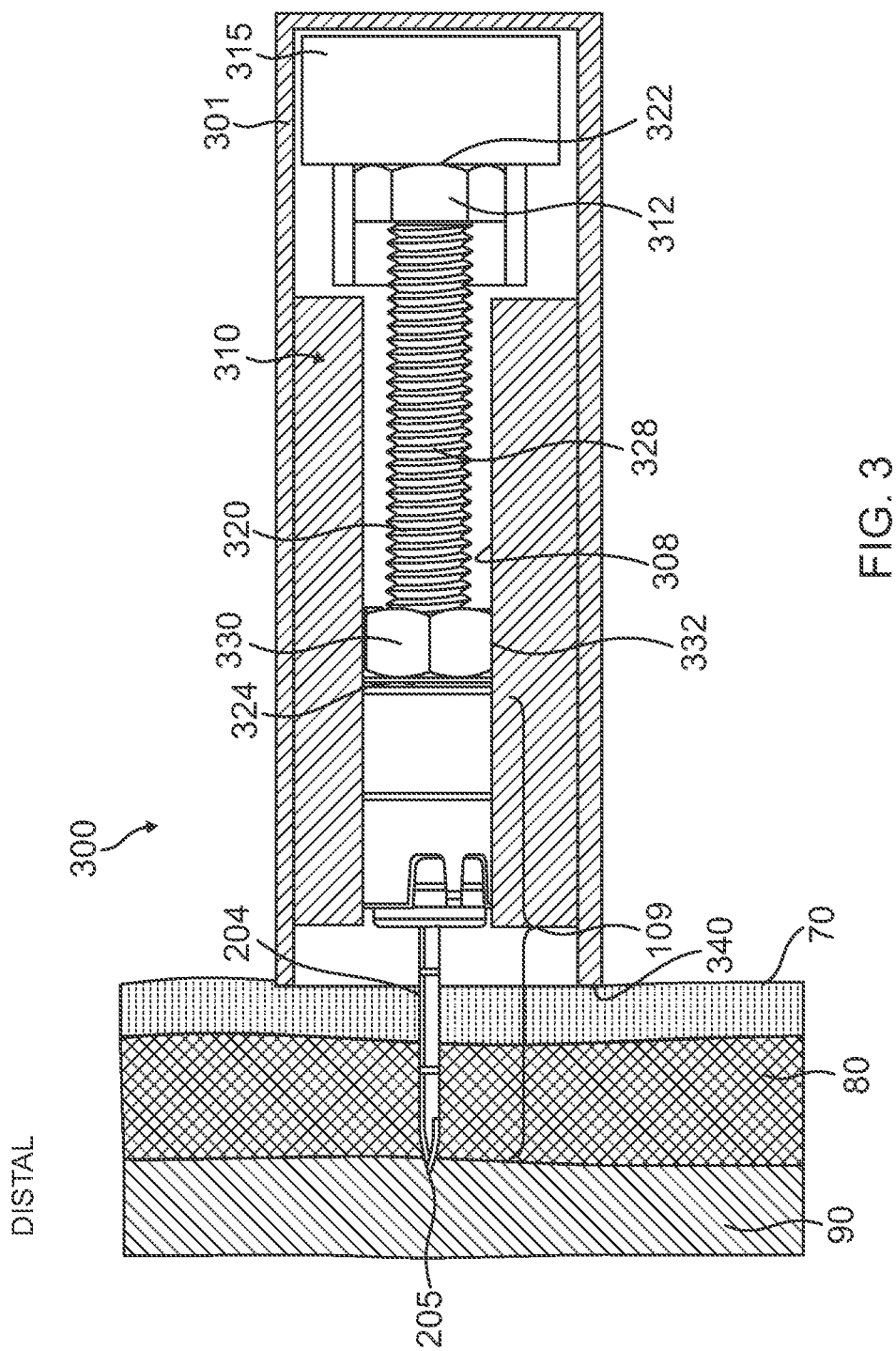
FIG. 3 illustrates an intraosseous access system, in accordance with embodiments disclosed herein.

FIG. 3 shows an embodiment of an intraosseous access system 300, including a driver 301, an energy source 315, and an advancement assembly 310. The advancement assembly includes a drive screw 320 extending from a proximal end 322 to a distal end 324. The drive screw 320 includes a threaded portion 328 and a drive screw head 312 disposed at a proximal end thereof. The drive screw 320 is coupled with an energy source 315 such that the energy source 315 can cause the drive screw 320 to rotate about a longitudinal axis. As described herein the energy source 315 can be an electric motor, torsion spring, or the like. The energy source 315 is fixed to a proximal end of the driver 301 such that the drive screw 320 remains stationary relative to the driver 301 along a longitudinal axis.

The drive screw 320 is threadably engaged with an access assembly access assembly nut 330, or similar female threaded structure that engages the male threaded portion 328 of the drive screw 320. The access assembly nut 330 defines one or more side facets 332 that engages an inner wall 308 of the driver 301 such that the access assembly nut 330 is prevented from rotating about a longitudinal axis but is able to slide along a longitudinal axis, relative to the driver 301. An access assembly 109 is coupled to a distal surface of the access assembly nut 330 and optionally includes socket 113, or the like, to secure the access assembly 109 to the access assembly nut 330.

In use, a distal end 340 of the driver 301 is positioned against the skin surface 70 of the patient and the energy source 315 is activated. As discussed herein, the energy source is trigger activated, pressure activated, or combinations thereof. The energy source 315 rotates the drive screw 320 which engages the access assembly nut 330 and drives the access assembly nut 330 and access assembly 109 in a distal direction relative to the driver 301. The energy source 315 continues to rotate the drive screw 320 until the access assembly nut 330 reaches a distal end 324 of the threaded portion 328 and prevents any further distal advancement. In an embodiment, the intraosseous access system 300 includes a switch that shuts off the energy source 315, e.g. an electric motor, when the access assembly nut 330 advances a predetermined distance. It will be appreciated that the distance of distal travel of the access assembly nut 330 and access assembly 109 is sufficient to advance the needle tip 205 through the bone cortex 80 to access the medullary cavity 90, i.e. to provide fluid communication between a lumen of the needle and the medullary cavity 90.

FIGS. 4A-4B shows an embodiment of an intraosseous access system 400, including a driver 401, an energy source 415, and an advancement assembly 410. FIG. 4A shows a retracted position before deployment, FIG. 4B shows a deployed position when the needle has been inserted into the medullary cavity 90. The advancement assembly 410 includes a drive screw 420 extending from a proximal end 422 to a distal end 424 and including a threaded portion 428. The drive screw 420 is attached to the driver 401 so as to prevent any relative movement between the drive screw 420 and the driver 401. A access assembly nut 430 is rotatably coupled with an energy source 415, e.g. electric motor, torsion spring, etc. such that when the energy source 415 is activated, the access assembly nut 430 is rotated relative to the drive screw 420. An access assembly 109 is coupled to a distal surface of the access assembly nut 430 and optionally includes socket 113, or the like, to secure the access assembly 109 to the access assembly nut 430. In an embodiment, the access assembly nut 430 is slidably engaged with the energy source 415 such that the access assembly nut 430 can move along a longitudinal axis relative to the energy source 415. In an embodiment, the energy source 415 is slidably engaged with the driver 401 such that the energy source 415 and access assembly nut 430 can move together along a longitudinal axis relative to the driver 401.

In use, a distal end 440 of the driver 401 is positioned against the skin surface 70 of the patient and the energy source 415 is activated. As discussed herein, the energy source is trigger activated, pressure activated, or combinations thereof. The energy source 415 rotates the access assembly nut 430 and advancement assembly 109 together. The access assembly nut 430 engages the threaded portion 428 of the drive screw 420 and advances the access assembly nut 430 and advancement assembly 109 in a distal direction relative to the driver 401.

The energy source continues to rotate the access assembly nut 430 until the access assembly nut 430 reaches a distal end 424 of the threaded portion 428 and prevents any further distal advancement. In an embodiment, the intraosseous access system 200 includes a switch that shuts off the energy source 415, e.g. an electric motor, when the access assembly nut 430 advances to a predetermined position. It will be appreciated that the distance of distal travel of the access assembly nut 430 and access assembly 109 is sufficient to advance the tip of the needle 204 a predetermined distance, through the cortex 80 of the bone to access the medullary cavity 90.

Figure 5:
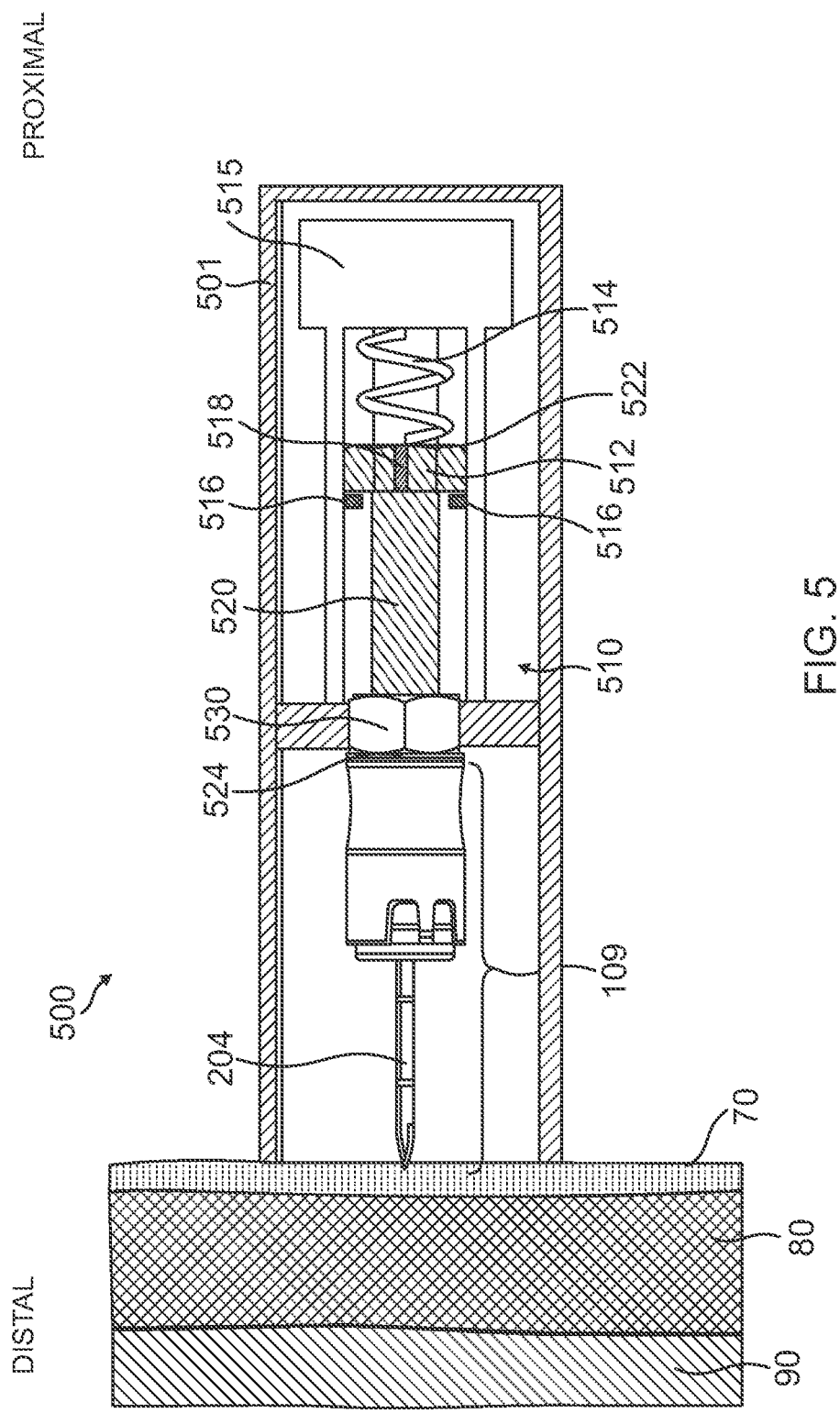
FIG. 5 illustrates an intraosseous access system, in accordance with embodiments disclosed herein.

FIG. 5 shows an embodiment of an intraosseous access device 500, including a driver 501, an energy source 515, and an advancement assembly 510. The advancement assembly 510 includes a drive bolt 520, extending from a proximal end 522 to a distal end 524. The drive bolt 520 includes a bolt head 512 disposed at a proximal end 522 and an access assembly 109 coupled to a distal end 524. Optionally, the access assembly 109 is coupled to the drive bolt 520 using socket 113. The drive bolt 520 is slidably engaged with a housing nut 530, or similar annular structure that surrounds the shaft of bolt 520. The housing nut 530 is attached to the driver 501 so as to prevent any relative movement between the housing nut 530 and the driver 501.

A compression spring 514, or similar biasing member, is compressed between a proximal surface of the bolt head 512 and proximal portion of the driver 501, or energy source 515. The spring 514 and bolt head 512 are held in place by a locking mechanism such as one or more protrusions 516. The locking mechanism can transition between a locked position where distal longitudinal movement of the drive bolt 520 is inhibited, and an unlocked position where the drive bolt 520 can slide longitudinally. In a locked position, the protrusions 516 engage a distal surface of the drive bolt head 512 to inhibit distal longitudinal movement. In the unlocked position, the protrusions 516 are aligned with slots 518 extending longitudinally through the drive bolt head 512 and configured to allow the protrusions to slide therethrough. In an embodiment, the drive bolt 520 can be rotated between a locked position and an unlocked position.

In use, the energy source 515 is activated, either by a trigger or pressure activation as described herein. The energy source 515 rotates the bolt head 512 about a longitudinal axis until the protrusions 516 align with the slots 518. This allows the bolt head 512 to slide, relative to the driver 501, along a longitudinal axis. This also allows the compression spring 514 to expand, urging the drive bolt 520 and access assembly 109 in a distal direction for a predetermined distance, until the bolt head 512 abuts against the housing nut 530, preventing any further distal movement. This forces the needle 204 a predetermined distance through the bone cortex 80 until a distal tip thereof extends sufficiently into the medullary cavity 90. It will be appreciated that other locking mechanisms configured to retain the bold head 512 in the retracted position are also contemplated. Exemplary locking mechanisms can include retractable protrusions that slide radially outward perpendicular to the longitudinal axis, pawls, ratchets, catches, grips, combinations thereof, or the like configured to release the bolt head 512 and allow the spring 514, or similar biasing member, to urge the access assembly 109 distally.

Figure 6:
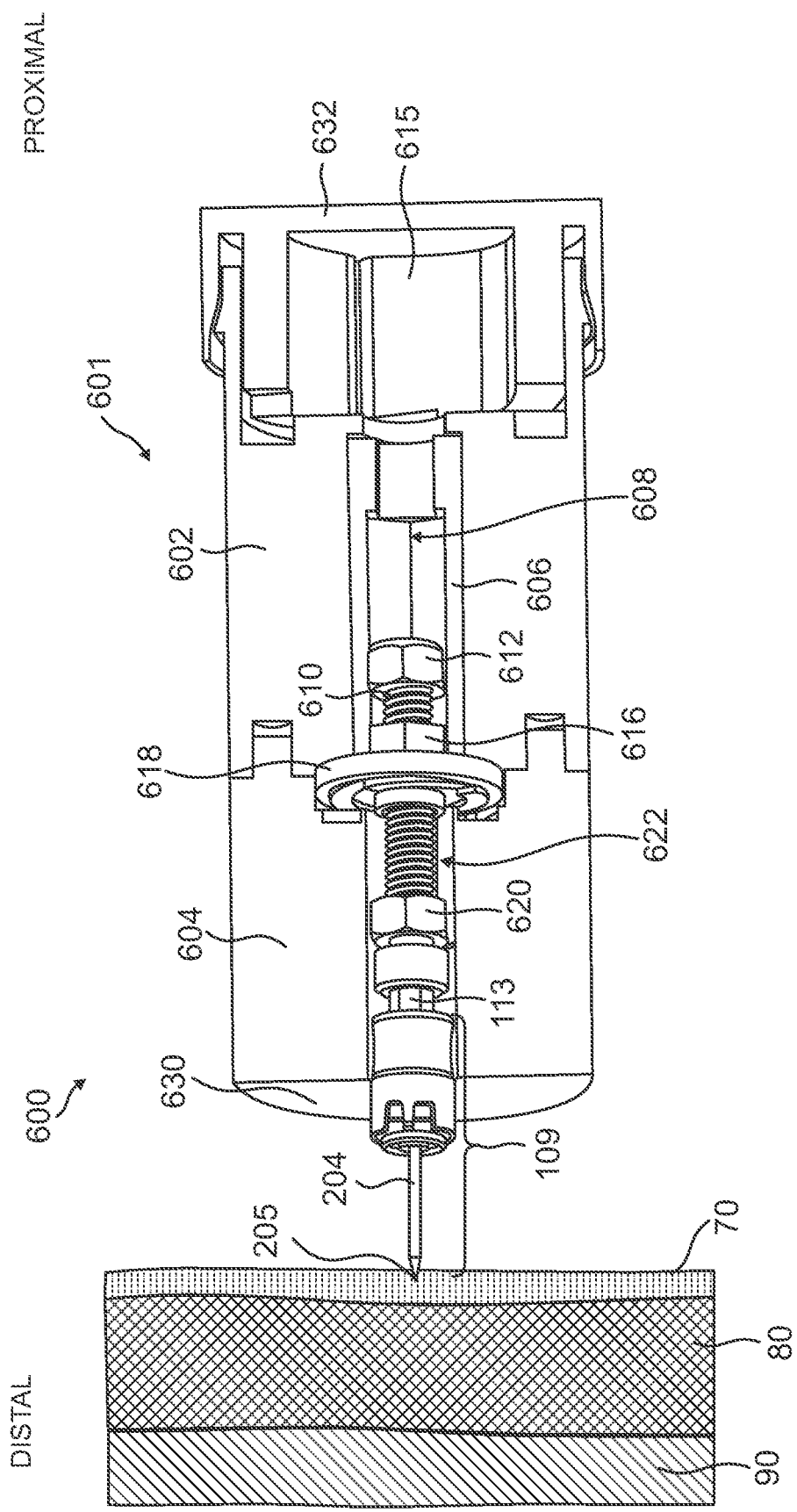
FIG. 6 illustrates an intraosseous access system, in accordance with embodiments disclosed herein.

FIG. 6 shows an embodiment of an intraosseous access system 600, which includes a spring driven energy source and a pressure trigger. The intraosseous access system 600 includes an upper housing 602 that engages a lower housing 604 to form a body of driver 601. The driver 601 is substantially radially symmetrical about a longitudinal axis. The upper housing 602 includes an energy source 615, e.g. a drive spring, and a drive spindle 606 that is coupled to the drive spring energy source 615. In an embodiment, the drive spring is a torsion spring, however it will be appreciated that the energy source 615 can also include flat springs, clock springs, electrical motors, and the like, without limitation.

The upper housing 602 and the drive spindle 606 are rotatably engaged such that when the drive spring energy source 615 is activated the drive spindle 606 can rotate freely within the upper housing 602. The drive spindle 606 further includes a centrally disposed, cylindrically shaped cavity 608. A cross-sectional area of the drive spindle cavity 608, extending normal to the longitudinal axis, defines a substantially hexagonal shape that is configured to receive a drive screw head 612. It will be appreciated that the cross-sectional shape of the drive spindle cavity 608 can also include other faceted polygonal cross sectional shapes that are configured to receive the drive screw head 612. In an embodiment, the drive screw head 612 is formed as a single unitary structure with the drive screw 610. In an embodiment, the drive screw head 612 includes a locking nut (not shown) that is threadably engaged with the drive screw 610 and fixed in place so as not to move relative to the drive screw 610. Accordingly, when the drive spring 615 is activated, the drive spindle 606 engages the drive screw head 612 and rotates the drive screw 610. The drive spindle cavity 608 allows the drive screw head 612 to slide relative to the drive spindle 606 along the longitudinal axis.

A distal end of the drive screw 610 engages socket 113, which in turn engages access assembly 109. A housing nut 616 is threadably engaged with the drive screw 610. The housing nut 616 is fixed within the upper housing 602, lower housing 604, or combinations thereof, so as not to move relative to the driver 601. Accordingly, as the drive screw 610 rotates about the longitudinal axis, the threaded engagement with the housing nut 616 causes the drive screw, and access assembly 109, to move longitudinally relative to the driver 601. In an embodiment, the drive screw 610 can advance distally along the longitudinal axis, until the drive screw head 612 engages the housing nut 616, inhibiting further distal movement. In embodiments, the drive screw can advance a predetermined distance. In an embodiment, the predetermined distance can be between 1 cm and 3 cm, however lesser or greater distances are also contemplated.

The lower housing 604 further includes a centrally disposed, cylindrically shaped cavity 622. A cross-sectional area of the lower housing cavity 622, extending normal to the longitudinal axis, defines a substantially hexagonal shape that is configured to slidably receive a drive nut 620. It will be appreciated that the cross-sectional shape of the lower housing cavity 622 can also include other faceted, polygonal, cross-sectional shapes that are configured to receive the drive nut 620. The drive nut 620 is threadably engaged with the drive screw 610 and disposed adjacent a distal surface of a locking piece 618. Accordingly, when the drive screw 610 rotates, the drive nut 620 is prevented from rotating by the engagement between a facet of the drive nut 620 and a wall surface of the lower housing cavity 622. However, the drive nut 620 is capable of sliding along a longitudinal axis relative to the lower housing 604.

A locking piece 618 is disposed between the drive spindle 606 and the lower housing 604. The locking piece 618 is fixedly attached with a distal end of the drive spindle 606 to prevent any movement of the drive spindle 606 relative to the locking piece 618. Further, the locking piece 618 can transition between a locked position and an unlocked position. For example, a distal surface of the locking piece 618 includes a star ratchet that releasably engages a proximal surface of the lower housing 604. The engagement between the locking piece 618 and the lower housing 604, i.e. the locked position, can be maintained by a biasing member (not shown), which applies a longitudinal distal pressure to locking piece 618, holding it against the lower housing 604, biasing the locking piece 618 towards a locked position. It will be appreciated that the engagement between the distal surface of the locking piece 618 and the proximal surface of the lower housing 604 can include a variety of locking mechanisms, for example, protrusions, detents, recesses, hex-key engagement, or similar "lock and key" engagement, or combinations thereof. Further, the locking piece 618 is slidably engaged with the drive screw 610 such that the drive screw 610 can move along a longitudinal axis relative to the locking piece 618. Accordingly, the locking piece 618 and the drive screw 610 can rotate relative to each other without causing any relative longitudinal movement therebetween.

In use, the intraosseous access system 600 is provided with the drive screw 610 in the retracted position, i.e. with the drive screw head 612 adjacent a proximal end of drive spindle cavity 608. The access assembly 109 is disposed within the lower housing cavity 622 with the drive nut 620 disposed adjacent the locking piece 618. In an embodiment, a distal tip 205 of needle 204 can extend beyond a distal surface 630 of the lower housing 604. In an embodiment, a distal tip 205 of needle 204 is disposed within the lower housing 604. The user can place the distal surface 630 of the driver 601 against the skin surface 70 of the patient. The tip 205 of the needle 204 penetrates the skin surface and contacts a surface of the bone cortex 80.

The user then applies sufficient pressure to the proximal surface 632 of the driver 601 so that the needle tip 205 presses against the bone cortex 80. This causes the drive screw 610 and drive nut 620 to slide, relative to the lower housing 604, and press against the locking piece 618. The locking piece can slide longitudinal and disengage the locking piece 618 from the lower housing 604. The energy source 615, e.g. drive spring, can then rotate the locking piece 618 and drive spindle 606 relative to the upper housing 602. The drive screw head 612 and drive screw 610 can then rotate relative to the driver 601, and engage the housing nut 616 to urge the drive screw 610 and access assembly 109 in a distal direction. This urges the needle 204 through bone cortex 80 so that the needle tip 205 can access the medullary cavity 90.

Advantageously, the pressure activation of the intraosseous access device 600 provides a quick and easy deployment of the access assembly 109. There is no need for any assembly of parts, needles, or the like and deployment involves only a single step process of aligning the needle tip and applying pressure to a proximal end 632. Further, applying pressure as such, stabilizes the device against the patient and provides sufficient counter-resistance to drive the needle 204 through the bone cortex 90. The rotation of the drive screw 612 causes the access assembly 109 to rotate, which also provides a drilling action, together with the distal force, and further facilitates driving the needle 204 through the bone cortex 80. In an embodiment, the coupling between the access assembly 109 and the drive screw 612 can allow for free rotation therebetween to offset and rotational movement and only provide distal force to provide a cleaner puncture through the bone cortex 80. Advantageously, an electric motor energy source 615 can provide a consistent force between the start and finish of the process. Advantageously, a spring driven energy source 615 can be stored for a longer time without loss of power, accordingly, intraosseous access systems 600 would not have to be replaced as often.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An autovance intraosseous access device, comprising:
   a housing;
   a drive screw, threadably engaged with the housing, the drive screw configured to advance a predetermined distance along a longitudinal axis;
   a drive spindle rotatably coupled to the housing and slidably engaged with the drive screw to allow the drive screw to advance along the longitudinal axis;
   a locking piece coupled to the drive spindle and transitionable between a locked position to inhibit rotation of the drive spindle and an unlocked position to allow the drive spindle to rotate about the longitudinal axis;
   a drive nut threadably engaged with the drive screw, slidably engaged with the housing and configured to engage the locking piece to transition the locking piece from the locked position to the unlocked position; and
   an access assembly coupled to a distal end of the drive screw, the access assembly comprising an obturator assembly, a shield, and a needle assembly.

2. The autovance intraosseous access device according to claim 1, further including a drive spring or an electric motor configured to rotate the drive screw.

3. The autovance intraosseous access device according to claim 1, further including a housing nut coupled with the housing in a fixed relationship and configured to threadably engage the drive screw with the housing.

4. The autovance intraosseous access device according to claim 1, wherein a distal surface of the locking piece includes a protrusion, recess, detent, hex-key engagement, star ratchet engagement, or "lock and key" engagement, configured to engage a surface of the housing in the locked position.

5. The autovance intraosseous access device according to claim 1, further including a drive screw head fixedly coupled to a proximal end of the drive screw and configured to engage the housing to inhibit further longitudinal movement of the drive screw.

6. The autovance intraosseous access device according to claim 1, wherein the predetermined distance is between 1 cm and 3 cm.

7. An intraosseous access device, comprising:
   a housing;
   a drive bolt slidably engaged with the housing along a longitudinal axis by a predetermined distance;
   a biasing member configured to urge the drive bolt distally;
   an access assembly coupled to a distal end of the drive bolt, the access assembly comprising an obturator assembly, a shield, and a needle assembly; and
   an energy source configured to rotate the drive bolt to transition the drive bolt between a locked position where longitudinal movement of the drive bolt is inhibited, and an unlocked position where the drive bolt can slide longitudinally.

8. The intraosseous access device according to claim 7, wherein the energy source is a drive spring or an electric motor.

9. The intraosseous access device according to claim 7, further including a protrusion engaging a surface of a bolt head of the drive bolt in the locked position and the protrusion aligning with a slot extending longitudinally through the bolt head in the unlocked position.

10. The intraosseous access device according to claim 7, wherein the drive bolt engages a portion of the housing or a housing nut to inhibit further distal movement along the longitudinal axis.

11. The intraosseous access device according to claim 7, wherein the predetermined distance is between 1 cm and 3 cm.

12. An intraosseous access device, comprising:
    a housing;
    a drive bolt slidably engaged with the housing along a longitudinal axis by a predetermined distance;
    a biasing member configured to urge the drive bolt distally;
    an access assembly coupled to a distal end of the drive bolt, the access assembly comprising an obturator assembly, a shield, and a needle assembly;
    an energy source configured to transition the drive bolt between a locked position and an unlocked position; and
    a protrusion engaging a surface of a bolt head of the drive bolt in the locked position, the protrusion aligning with a slot extending longitudinally through the bolt head in the unlocked position.

* * * * *